United States Patent [19]

Bonnard

[11] Patent Number: 4,927,270

[45] Date of Patent: May 22, 1990

[54] METHOD OF AND APPARATUS FOR DETERMINING MELTING POINTS

[76] Inventor: John A. Bonnard, P.O. Box 781393, Sandton, Transvaal, South Africa

[21] Appl. No.: 269,014

[22] Filed: Nov. 9, 1988

[30] Foreign Application Priority Data

Nov. 18, 1987 [ZA] South Africa .................. 87/8616

[51] Int. Cl.$^5$ ............................................ G01N 25/04
[52] U.S. Cl. .................................... 374/16; 374/17; 374/153; 374/154
[58] Field of Search .............. 374/16, 17, 18, 25, 374/26, 124, 139, 159, 160, 153, 154; 116/217

[56] References Cited

U.S. PATENT DOCUMENTS

| | | | |
|---|---|---|---|
| 2,669,863 | 2/1954 | Shapiro | 374/17 |
| 3,143,876 | 8/1964 | Wallgren | 374/17 |
| 3,153,337 | 10/1964 | Gilson et al. | 374/16 |
| 3,173,288 | 3/1965 | Davis et al. | 374/16 |
| 3,173,289 | 3/1965 | Davis | 374/16 |
| 3,501,580 | 3/1970 | Stingele | 374/17 |
| 3,718,757 | 2/1973 | Gulitz et al. | 374/124 |
| 3,941,923 | 3/1976 | Wheeler | 374/124 |
| 4,539,588 | 9/1985 | Ariessohn et al. | 374/124 |

FOREIGN PATENT DOCUMENTS

| | | | |
|---|---|---|---|
| 141461 | 4/1935 | Austria | 374/16 |
| 2517396 | 11/1975 | Fed. Rep. of Germany | 374/16 |
| 2708365 | 8/1978 | Fed. Rep. of Germany | 374/17 |
| 2485729 | 12/1981 | France | 374/124 |
| 56-27623 | 3/1981 | Japan | 374/124 |
| 61-217740 | 9/1986 | Japan | 374/16 |
| 851221 | 7/1981 | U.S.S.R. | 374/16 |
| 2202941 | 10/1988 | United Kingdom | 374/16 |

OTHER PUBLICATIONS

"Kofler Hotbench", pamphlet dated Jun. 1965.
"Kofler Thermopan and Micro Hot and Cold Stages", pamphlet dated May 1966.

*Primary Examiner*—Allan N. Shoap
*Assistant Examiner*—Diego F. F. Gutierrez
*Attorney, Agent, or Firm*—Young & Thompson

[57] ABSTRACT

The melting point of a powdery or particulate material is determined by allowing a sample of the material to contact a heated surface. If the material does not melt it is removed from the surface and the temperature of the surface is increased. The process is repeated until the material is observed to melt on the surface, the temperature of the surface at that time being observed in order to determine the melting point in question.

9 Claims, 1 Drawing Sheet

METHOD OF AND APPARATUS FOR DETERMINING MELTING POINTS

BACKGROUND OF THE INVENTION

This invention relates to a method of, and apparatus for, determining the melting point of a powdered material.

In the following description the invention will be described mainly with reference to determining the melting point of coal ash or, more generally, the combustion product of a combustible material. It is to be understood however that other products which are powdered or particulate, for example sugar, can also be used in the method and apparatus of the invention.

The melting point of ash that is produced when coal is combusted in a furnace is of great importance. If the temperature within the furnace exceeds the melting point of the ash then the ash melts and in the liquid form adheres to surfaces inside the furnace. If this process continues the interior of the furnace is ultimately closed off and the through-flow of mateial through the furnace is impeded and the efficiency of heat transfer drops. In a severe case the furnace must be shut down and the fused deposits on the internal surfaces of the furnace must be mechanically removed for example by chipping.

A standardised technique is used to assess the melting point of a combustion product. In this technique the coal which is under test is placed in a flat dish and slowly allowed to burn to an ash at a comparatively low temperature. The ash is ground, moistened, and moulded into a small three-sided pyramid. The pyramid is carefully dried under controlled conditions and then placed in a furnace the temperature of which is gradually increased.

An operator monitors the pyramid by means of a special viewing device and records temperatures at which various events occur; for example the temperature at which the uppermost sharp point of the pyramid rounds off perceptibly, the temperature at which the pyramid slumps to a certain extent by proportion, and the temperature at which the pyramid flows and rounds off to a molten bead.

The standardised procedure described is laborious and time consuming and is subject to inaccuracies which arise inter alia from the observer's skills and experience, and from variations in the pyramid-making process.

The requirement for a human observer has been obviated by making using of electronic scanners which view the pyramid under test, and by using computers to process the ensuing data. The problems associated with the forming of the pyramid however remain.

SUMMARY OF THE INVENTION

The invention provides a method of determining or assessing the melting point of a powdered, particulate or similar material which includes the steps of producing a heated surface, allowing a sample of the material to contact the heated surface, and observing the material on the surface to determine or assess the melting point thereof.

The sample of material may be allowed to settle on the heated surface, and may fall under the action of gravity.

The sample of material may be removed from the surface and be replaced by a fresh sample. This process may be repeated one or more times.

Material, especially non-melted material, on the surface may be removed in any suitable way. The surface may be inverted or be jarred, vibrated or be subjected to any other type of mechanical shock.

In one form of the invention the surface is maintained at a critical temperature. In a different form of the invention the surface is heated in a controlled manner and its temperature is gradually increased.

The material may be observed electronically, for example with the aid of a scanner, a camera or the like.

The heated surface may, if heated sufficiently, emit light. This aids in the viewing process. Alternatively if the surface does not emit light the method may include the step of illuminating the material on the surface.

The method described is suitable for determining or assessing the melting point of a large number of different types of materials. When a combustion product is to be placed under test then the raw material e.g. coal may be combusted in a primary step. For example the coal, in a suitable form, may be allowed to pass through a combustion chamber and at an exit from the chamber ash may be passed to the heated surface.

The invention also provides apparatus for determining or assessing the melting point of a powdered, particulate or similar material which includes a heated surface, means for causing the material to contact the heated surface, and means for observing the material to determine or assess the melting point thereof.

The material may be allowed to settle on the heated surface.

The surface may be heated in any suitable way. The surface may for example be heated electrically, inductively, by means of microwave heating, or the like. The heated surface for example may itself consist of an electrical element or the like.

The heated surface may be replaceable in the apparatus.

The temperature of the heated surface may be maintained at a critical value. In a different form of the invention the temperature of the heated surface is increased in a controlled manner. In either case this may be done using any suitable control device.

The observing means preferably comprises a scanning camera or the like. If inadequate light is emitted by the heated surface then means may be provided for illuminating the heated wire so that it can be observed better.

The aforementioned apparatus may be located in an insulated chamber.

If the apparatus is to be used for assessing or determining the melting point of a combustion product then the apparatus may be used in conjunction with a pre-combustion chamber or the like, arranged so that combustion products which are extracted from the combustion chamber pass directly to the heated surface.

BRIEF DESCRIPTION OF THE DRAWINGS

The invention is further described by way of example with reference to the accompanying drawing in which.

DESCRIPTION OF PREFERRED EMBODIMENT

Figure 1:
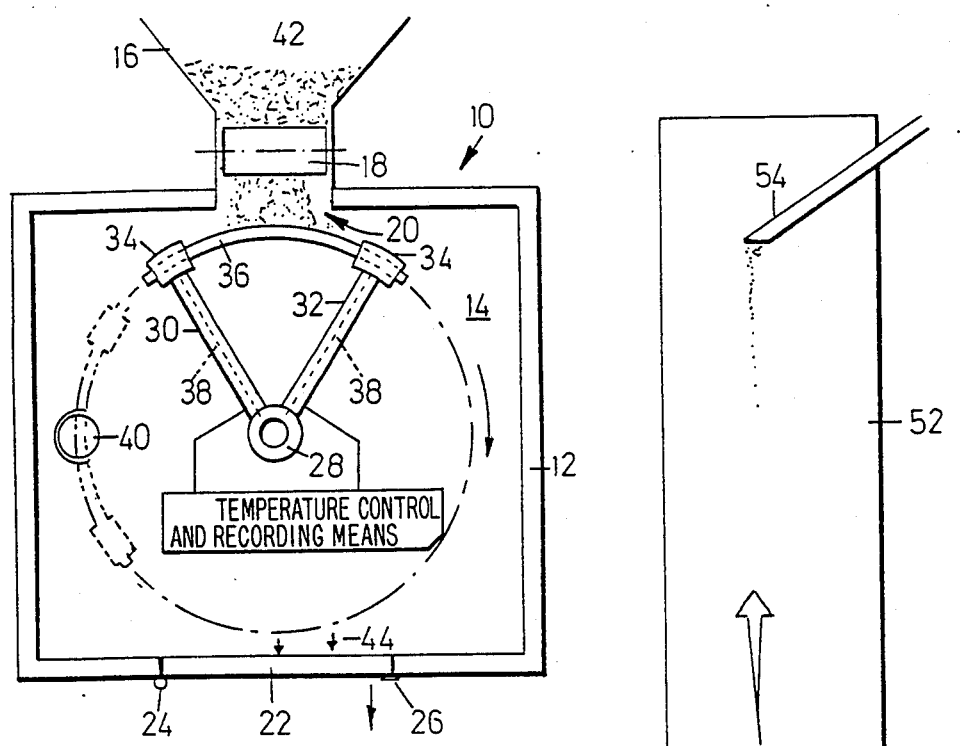
FIG. 1 is a schematic side view of apparaus according to one form of the invention for assessing the melting point of a combustion product.

FIG. 1 illustrates apparatus 10 according to one form of the invention which includes an insulated housing 12 which defines a chamber 14, a hopper 16 at an upper end of the housing, rollers 18 in a base of the hopper adjacent an inlet 20 into the chamber, a door 22 at a lower end of the housing which is pivotal about a hinge point 24 and which is retained in a closed position by means of a catch 26, a horizontal axle 28 inside the chamber 14, the axle being rotatable in a controlled manner by means of a motor, not shown, two radial supporting arms 30 and 32 which extend from the axle 28, each arm having clips 34 at its outer end, an electrically conductive wire 36 which is engaged with the clips and which extends from one arm to the other, electrical conductors 38 respectively inside the arms which extend to the clips 34 from a controllable electrical source, not shown, and an optical scanning arrangement inside the chamber and indicated schematically by the reference numeral 40.

The hopper 16, in this example, receives a sample 42 of ash the melting point of which is to be determined.

The axle 28 and the radial supporting arms which carry the wire 36 are rotated at a controlled speed by means of the motor. When the wire 36 is in the uppermost position shown in FIG. 1 the rollers 18 which are under the control of a suitable mechanism linked to the aforementioned rotating components, are rotated to feed through the inlet 20 a controlled quantity of the sample 42. The material falling from the inlet contacts and adheres to the upper surface of the wire 36.

The wire 36 is heated in a controlled manner to a particular temperature determined in accordance with the characteristics of the sample 42. In one form of the invention the wire is maintained at a critical temperature which may for example be related to the characteristics of a particular furnace. The behaviour of the material on the wire is then monitored at this particular temperature. In an alternative form of the invention designed to assess the melting point of the sample, the temperature of the wire is gradually increased. The temperature of the wire may be accurately controlled, to known values, merely by controlling the current which flows through the wire.

Assume for example that the sample 42 is ash and that the apparatus is being used to determine the melting point of the ash. The ash falls onto the heated wire 36 which is continuously rotating. When the wire 36 reaches a lowermost position opposite the door 22 a mechanical shock or vibratory movement is imparted to the axle 28 and the supporting arms 30 and 32. This may be effectively done for example by means of a suitable cam which is fixed to the axle 28 and which cyclically presents a suitably shaped surface to a cam follower when the wire is opposite the door. If the ash has not melted i.e. if the temperature of the wire is below the melting point of the ash then any ash on the wire is loosened and falls downwardly onto the door 22 is indicated by arrows 44. The wire then travels upwardly and passes the scanning arrangement 40 which automatically observed the wire to determine whether or not any of the ash has melted and turned into liquid beads.

At the uppermost position of the wire a further sample of the material is deposited on the upper surface of the wire and the process is repeated.

The wire temperature is continuously being increased. Thus ultimately a point is reached at which the ash on the wire starts melting and then adheres to the wire. If this happens the mechanical shock which is imparted to the wire does not dislodge the material from the wire and the adhering material is detected by the scanning arrangement 40. The temperature of the wire is noted at the same time. By use of suitable data processing techniques, and image comparative processes, the melting point of the ash can be determined using a computer based data storage and processing device. A device of this nature is known to those skilled in the art and thus its construction, and method of operation, has not been detailed herein.

When the process is complete the door 22 is opened to remove the ash lying on the floor of the housing.

In many instances the heated wire 36 will produce adequate light for the scanning arrangement 40 to operate effectively. However if the emitted light intensity is too low then artificial lighting may be used to illuminate the wire adequately. For example if the sample 42 consists of sugar which has a low melting point then normally additional lighting means will be employed.

Figure 2:
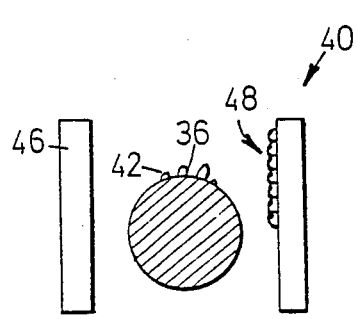
FIG. 2 is an enlarged view of portion of the apparatus of FIG. 1 and at right angles thereto.

FIG. 2 illustrates schematically and on an enlarged scale the wire 36 in cross section. Material 42 on an upper surface of the wire has started melting and therefore adheres to the wire. In this instance use is made of an illuminated panel 46 to provide a suitable background for a diode array 48 which constitutes the scanning arrangement. The diode array 48 is pulsed so that the shape of the material, directly opposite the array 48 is assessed for each angular step of movement of the wire past the ray. The data collected in this way is transmitted to a computer for analysis.

With the arrangement shown in FIG. 1 the sample 42 may be a combustion product or alternatively is of a nature for example sugar such that prior combustion threof is not required. If the melting point of a combustion product such as coal is to be determined then powdered coal can be fed directly into a combustion chamber in the manner illustrated in FIG. 3.

Figure 3:
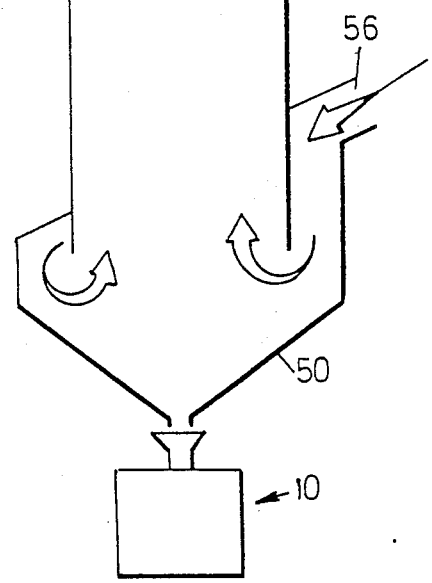
FIG. 3 is a view of a variation of the invention based on the apparatus shown in FIG. 1.

In the FIG. 3 embodiment use is made of apparatus 10 which is substantially similar to that shown in FIG. 1. Mounted above the inlet 20 and the hopper 16 is a funnel 50 which is topped by a combustion column 52. Powdered coal which is to be combusted is fed into the upper end of the column from an inlet 54. A combustion gas is introduced into a lower region of the funnel through an inlet 56. The gas flows upwardly through the column and causes combustion of the downwardly falling coal. The ash produced in the combustion process falls downwardly and is collected by the funnel 50 and then channelled to the apparatus 10 whereupon the melting point of the ash is determined in the manner described.

It is apparent that the principles described can be implemented in a variety of ways. For example the heated wire can be replaced by any suitable heated surface. It is not essential to have the wire rotated about a horizontal axis and any other type of suitable movement could instead be adopted. The mechanical jarring of the wire to remove excess material when the wire is at a lowermost position can be carried out in a variety of ways as well. Similarly the optical scanner 40 which has been described in FIG. 2 as consisting of an array of diodes can be replaced by a television camera or any other sensing device.

The essence of the invention lies in the provision of a surface which is heated in a controlled manner and which is brought into contact with a sample of the material which is under test. The sample is monitored, preferably automatically, and the temperature at which the sample melts is automatically recorded. It is apparent that, if desired, the sample can even be monitored manually.

The technique adopted by the invention makes it possible for example to monitor on-line pulverised coal which is fed to a boiler or other furnace system. Thus the wire 36 can be maintained at a critical temperature that represents the required fusibility minima for the feed material, related to the combustion temperature. If the apparatus detects the commencement of ash fusion in the feed material at the critical temperature then a warning system can be activated.

The use of an electrically resistive wire 36, which is inexpensive, makes it possible simply to replace the wire with a fresh wire once the material under test has fused and set and consequently adhered to the wire.

I claim:

1. A method of determining the melting point of a powdered or particulate material which includes the steps of producing a heated surface, gradually increasing the temperature of the heated surface, causing a succession of samples of the material to contact the heated surface and moving the heated surface in between the loading of the succession of samples to discharge from the heated surface unmelted powdered or particulate material remaining from a preceding sample, and observing each sample of the material on the heated surface to detect whether the respective sample of the material melts on the heated surface.

2. A method according to claim 1, wherein each sample of the material is allowed to settle under gravity action onto the heated surface.

3. A method according to claim 1, wherein the sample of the material is fed to the heated surface, in a controlled manner, from a container of the material.

4. A method according to claim 1, wherein each unmelted sample of material is removed from the heated surface and a fresh sample of the material is then caused to contact the heated surface.

5. A method according to claim 1, which includes the step of illuminating the heated surface.

6. A method according to claim 1, wherein melting of a sample of the material is detected by observing when adhesion of the sample of the material, to the heated surface, takes place.

7. Apparatus for determining the melting point of a powdered or particulate material which includes a container for the material, a surface, means for heating the surface to a desired temperature in a controlled manner, means for effecting relative movement between the surface and the container, means for releasing a plurality of samples of the material from the container to move successively under gravity action onto the heated surface, means for displacing unmelted material from the heated surface before a subsequent sample of the material moves onto the heated surface, and means for recording the temperature of the heated surface at which the material melts.

8. Apparatus according to claim 7, wherein the heated surface is a surface of a replaceable electrical element.

9. A method of determining the melting point of a powdered or particulate material which includes the steps of producing a heated surface, allowing a sample of the material to contact the heated surface, if the sample of the material has not melted then removing the sample of the material from the heated surface, increasing the temperature of the heated surface, and repeating the aforementioned steps with successive fresh samples and moving the heated surface in between the loading of the successive fresh samples to discharge from the heated surface unmelted powdered or particulate material remaining from a preceding sample until a respective sample is observed to melt on the heated surface, and measuring the temperature of the heated surface.

* * * * *